(12) United States Patent
Prasad et al.

(10) Patent No.: US 9,201,025 B2
(45) Date of Patent: Dec. 1, 2015

(54) ABSOLUTE NUCLEAR MATERIAL ASSAY USING COUNT DISTRIBUTION (LAMBDA) SPACE

(75) Inventors: Manoj K. Prasad, Pleasanton, CA (US); Neal J. Snyderman, Berkeley, CA (US); Mark S. Rowland, Alamo, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 810 days.

(21) Appl. No.: 13/456,032

(22) Filed: Apr. 25, 2012

(65) Prior Publication Data

US 2012/0303291 A1 Nov. 29, 2012

Related U.S. Application Data

(63) Continuation of application No. 12/480,562, filed on Jun. 8, 2009, now Pat. No. 8,194,813, which is a continuation-in-part of application No. 11/244,088, filed on Oct. 4, 2005, now Pat. No. 7,756,237.

(60) Provisional application No. 60/620,304, filed on Oct. 19, 2004.

(51) Int. Cl.
*G01N 23/05* (2006.01)
*G01N 23/00* (2006.01)
*G01T 3/00* (2006.01)

(52) U.S. Cl.
CPC .............. *G01N 23/005* (2013.01); *G01T 3/00* (2013.01)

(58) Field of Classification Search
USPC .......................................................... 376/153
See application file for complete search history.

(56) References Cited

U.S. PATENT DOCUMENTS

| 3,456,113 A | 7/1969 | Keepin |
| 3,707,631 A | 12/1972 | Untermyer |
| 3,723,727 A | 3/1973 | Wogman |
| 3,736,429 A | 5/1973 | Foley |
| 4,201,912 A | 5/1980 | Evans et al. |
| 4,483,816 A | 11/1984 | Caldwell et al. |
| 4,617,466 A | 10/1986 | Menlove et al. |
| 4,920,271 A | 4/1990 | Arnone |
| 5,197,130 A | 3/1993 | Chen et al. |
| 6,341,150 B1 | 1/2002 | Ivanov et al. |

(Continued)

FOREIGN PATENT DOCUMENTS

JP 06300887 A 10/1994

OTHER PUBLICATIONS

Hicks, et al., "Probablilities of Prompt-Neutron Emission From Spontaneous Fission", Phys. Rev. vol. 101, No. 3, pp. 1016-1020 (Feb. 1, 1956).

(Continued)

*Primary Examiner* — Jack W Keith
*Assistant Examiner* — Sean P Burke
(74) *Attorney, Agent, or Firm* — Staniford Tomita

(57) ABSTRACT

A method of absolute nuclear material assay of an unknown source comprising counting neutrons from the unknown source and providing an absolute nuclear material assay utilizing a model to optimally compare to the measured count distributions. In one embodiment, the step of providing an absolute nuclear material assay comprises utilizing a random sampling of analytically computed fission chain distributions to generate a continuous time-evolving sequence of event-counts by spreading the fission chain distribution in time.

6 Claims, 8 Drawing Sheets

(56) References Cited

U.S. PATENT DOCUMENTS

| | | |
|---|---|---|
| 6,420,712 B1 | 7/2002 | Menlove et al. |
| 6,509,563 B1 | 1/2003 | McElroy, Jr. et al. |
| 2002/0125439 A1 | 9/2002 | Caldwell et al. |
| 2005/0105665 A1 | 5/2005 | Grodzins et al. |

OTHER PUBLICATIONS

Furuhashi, et al., "Third Moment of the Number of Neutrons Detected in Short Time Intervals", Journal of Nuclear Science and Technology, 5 (2), pp. 48-59 (Feb. 1968).

Hage, et al., "Correleation Analysis with Neutron Count Distributions in Randomly or Signal Triggered Time Intervals for Assay of Special Fissile Materials", Nuclear Science and Engineering, 89, pp. 159-176 (1985).

Prasad, et al., "Statistical Theory of Fission Chains and Generalized Poisson Neutron Counting Distributions", University of California, LLNL, pp. 1-38 (Aug. 6, 1991).

Ensslin, et al., "Applications Guide to Neutron Multiplicity Counting", LA__13422-M, UC-700, Los Alamos National Laboratory, (Nov. 1998).

Prasad, et al., "Statistical Theory of Fission Chains and Generalized Poisson Neutron Counting Distributions", University of California, LLNL, pp. 1-41 (Apr. 16, 2002).

Esarda, NCC, "Passive Neuton Coincidence Counting Teachniques for PU Mass Determination", (Mar. 1, 2004).

Frank, et al., "Application of Neutron Correlation Techniques to Warhead Authentication", Feasability and Conceptual Requirements—Monte Carlo Simulations and Statistical Analysis, UCRL-TR-206043 (Aug. 13, 2004).

ABSOLUTE NUCLEAR MATERIAL ASSAY USING COUNT DISTRIBUTION (LAMBDA) SPACE

CROSS-REFERENCE TO RELATED APPLICATIONS

This application is a Continuation of U.S. patent application Ser. No. 12/480,562 filed on Jun. 8, 2009, which is a Continuation-In-Part of U.S. patent application Ser. No. 11/244,088 filed on Oct. 4, 2005, now U.S. Pat. No. 7,756,237 issued Jul. 13, 2010, and entitled "Absolute Nuclear Material Assay," and which in turn claims the benefit of U.S. Provisional Patent Application No. 60/620,304 filed by Manoj Prasad, Neal J. Snyderman, and Mark S. Rowland Oct. 19, 2004 and titled "Absolute Nuclear Material Assay." U.S. Provisional Patent Application No. 60/620,304 is incorporated herein by this reference.

STATEMENT REGARDING FEDERALLY SPONSORED RESEARCH

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present invention relates to nuclear material assay and more particularly to an absolute nuclear material assay.

BACKGROUND

United States Patent Application No. 2005/0105665 by Lee Grodzins and Peter Rothschild for a system of detection of neutrons and sources of radioactive material, published May 19, 2005, provides the following state of technology information: "There is a need to find sources of radiation and other nuclear material that are clandestinely transported across national boundaries. The sources of clandestine nuclear material may be in the form of "dirty bombs" (e.g., a conventional explosive combined with radioactive nuclides designed to spread radioactive contamination upon detonation), fissile material, and other neutron and radiation emitting sources that may present a hazard to the public. During recent years, the United States government has placed mobile vehicles at strategic areas with gamma ray detectors dedicated to the task of finding fissile material. Atomic explosives may be made from $^{235}$U, a rare, naturally occurring, isotope of uranium that lives almost $10^9$ years, or $^{239}$Pu, a reactor-made isotope that lives more than $10^4$ years. $^{235}$U decays with the emission of gamma ray photons (also referred to as 'gammas'), principally at 185.6 keV and 205.3 keV. $^{239}$Pu emits a number of gamma rays when it decays, the principal ones being at 375 keV and 413.7 keV. These gamma rays are unique signatures for the respective isotopes, but fissile material invariably contains other radioactive isotopes besides those essential for nuclear explosives. For example, weapons grade uranium may contain as little as 20% $^{235}$U; the rest of the uranium consists of other isotopes. The other uranium and plutonium isotopes reveal their presence by gamma rays emitted by their daughters. For example, a daughter of $^{238}$U emits a high energy gamma ray at 1,001 keV; a daughter of $^{232}$U, an isotope present in fissile material made in the former USSR, emits a very penetrating gamma ray at 2,614 keV; and a daughter of $^{241}$Pu emits gamma rays of 662.4 keV and 722.5 keV."

U.S. Pat. No. 4,201,912 issued May 6, 1980 to Michael L. Evans et al and assigned to The United States of America as represented by the United States Department of Energy, provides the following state of technology information: "A device for detecting fissionable material such as uranium in low concentrations by interrogating with photoneutrons at energy levels below 500 keV, and typically about 26 keV. Induced fast neutrons having energies above 500 keV by the interrogated fissionable material are detected by a liquid scintillator or recoil proportional counter which is sensitive to the induced fast neutrons. Since the induced fast neutrons are proportional to the concentration of fissionable material, detection of induced fast neutrons indicates concentration of the fissionable material."

U.S. Pat. No. 4,617,466 issued Oct. 14, 1986 to Howard O. Menlove and James E. Stewart and assigned to The United States of America as represented by the United States Department of Energy, provides the following state of technology information: "Apparatus and method for the direct, nondestructive evaluation of the .sup.235 U nuclide content of samples containing UF.sub.6, UF.sub.4, or UO.sub.2 utilizing the passive neutron self-interrogation of the sample resulting from the intrinsic production of neutrons therein. The ratio of the emitted neutron coincidence count rate to the total emitted neutron count rate is determined and yields a measure of the bulk fissile mass. The accuracy of the method is 6.8% (1.sigma.) for cylinders containing UF.sub.6 with enrichments ranging from 6% to 98% with measurement times varying from 3-6 min. The samples contained from below 1 kg to greater than 16 kg. Since the subject invention relies on fast neutron self-interrogation, complete sampling of the UF.sub.6 takes place, reducing difficulties arising from inhomogeneity of the sample which adversely affects other assay procedures."

U.S. Pat. No. 3,456,113 issued Jul. 15, 1969 to G. Robert Keepin provides the following state of technology information: "An apparatus and method of detecting, identifying and quantitatively analyzing the individual isotopes in unknown mixtures of fissionable materials. A neutron source irradiates the unknown mixture and the kinetic behavior of the delayed neutron activity from the system is analyzed with a neutron detector and time analyzer. From the known delayed neutron response of the individual fission species it is possible to determine the composition of the unknown mixture. Analysis of the kinetic response may be accomplished by a simple on-line computer enabling direct readout of isotopic assay."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

A neutron is created by a physical process, either fission or an inducing nuclear reaction. The created neutron or neutrons then interact with the environment. If the environment contains more nuclear material (i.e., uranium), the first neutrons may create more neutrons by causing more fission or other nuclear reactions. The first and second and subsequent neutrons are a chain. A chain may start with an alpha particle creating a single neutron that subsequently creates hundreds of fissions. Another chain may start with a spontaneous fission creating three neutrons that go on to create hundreds of fissions. These chains evolve over time and some of the neutrons are absorbed or lost. Some members of the chain may be finally captured in a neutron detector device. The final captured neutrons may be counted as a simple sum or observed as a time dependent rate. What may start out as a chain of 1000 neutrons may result in a count of two neutrons during some period of time, in a detector.

The observed count data is used to derive certain relevant physical parameters regarding the source of the neutrons. The physical parameters may include the mass, multiplication, alpha ratio, efficiency, and time constant associated with the neutrons. In this case there are five different parameters, although other numbers of parameters are also possible. Describing the chains, with all the numerical detail requires a way to relate the five physical parameters to how the chains are created. In general, current techniques of relating the relevant physical parameters to an observed quantity (e.g., how many 2's are observed) are based on approximations in certain prior art systems.

Embodiments of the present invention provide a system of absolute nuclear material assay of an unknown source. These embodiments provide a system that relates, in detail, a correlated or uncorrelated chain of neutrons with what appears in a detector or other instrument, that is, they relate a physical parameter or parameters of the unknown source to a measured quantity from the unknown source. How the chain of neutrons is used was traditionally related in a process that connects count sums to physical parameters of interest, such as multiplication. The limitations of prior art start with and are rooted in approximations in the detailed description of the neutron chain. These approximations, in the details of exactly how a chain is described and evolves in time, conspire to make the current known process of relating chains to physical parameters highly unstable. Methods in the prior art therefore rely on a process of calibration. For example, calibration means that of the five parameters needed to describe a physical system, four are determined independent of an assay measurement. The old assay process then proceeds by assuming the four parameters apply and are considered with a measurement of the fifth parameter, to be extracted from the assay measurement.

According to embodiments of the present invention, the assay solution comes from the solution of a coupled set of equations where all five parameters are used to solve for a physical parameter of interest, such as multiplication. The present invention benefits from a complete understanding of an arbitrary chain and variously allows the extraction all five parameters, or four parameters given only one, or three parameters given only two, and so on.

In an embodiment, neutrons are measured in a neutron detector and five parameters are determined that describe the object that is being assayed. These parameters comprise the mass, multiplication, alpha ratio, efficiency, and time constant, although the invention is not so limited. The present invention makes an assay for the purpose of determining these five parameters, given that one does not know these five parameters. Other parameters may include, but are not limited to: background contributions, external sources adding counts, (n,2n) neutron sources, and so on.

The present invention provides a method of absolute nuclear material assay of an unknown source comprising counted neutrons from the unknown source and uses a theoretical model to optimally fit the measured count distribution. The present invention begins by analytically solving for and efficiently computing the entire fission chain probability distribution for any given set of physical parameters (e.g., mass, multiplication, alpha ratio, efficiency, and time constant). This fission chain distribution is then used to simulate a data stream from which time dependent count distributions are constructed. The model randomly initiates fission chains at a rate dependent on the measured source strength and samples from the analytical fission chain probability distributions to artificially create data with statistical fluctuations with finite time counting. This approach allows the most direct modeling of the data as it is actually taken. It also allows complete control in modeling issues related to finite sampling, truncation errors from inherently truncated data, and dead time effects in the detector.

In general, known prior art systems could only compute the first few moments of the full idealized fission chain distribution and relate these to moments of measured data. These previous systems are fundamentally flawed in modeling finite sample truncated data with idealized infinite population moments. This flaw manifests itself in an erratic and unstable reconstruction of the unknown physical parameters. In contrast, the approach of the present invention is based on analytical fission chain probability distribution, and is thus able to robustly and stably reconstruct physical parameters.

Also of significance is that embodiments of the present invention provide a complete theoretical framework for modeling the entire neutron count distribution, not just its first few moments. Any measured count distribution and its model made with the five, or even more parameters, may be quantitatively compared for the purpose of optimally reverse engineering the five or more parameters that describe the unknown. Prior systems based on the first few moments can only get at some small subset of the information contained in the data, and even then is flawed by issues of finite sample size and truncation errors.

The present invention provides a method of absolute nuclear material assay of an unknown source comprising counting neutrons from the unknown source and providing an absolute nuclear material assay utilizing a sampling method to distribute theoretical count distributions over time. The method utilizes a random sampling of a count distribution to generate a continuous time-evolving sequence of event-counts by spreading the count distribution in time. The present invention also provides an apparatus for absolute nuclear material assay comprising a multigate neutron multiplicity counter, a processor that solves three moment equations, a processor that provides fit to actual time dependence of the moments to get proper asymptotic moments, a processor that uses the estimated parameters to compute full count distribution, a processor that compares truncated data moments with untruncated and truncated theoretical moments, and a processor that provides adjustments to reduce bias.

The present invention has use in providing an assay of nuclear material. The present invention also has uses in providing the amount of moderator and in providing a neutron lifetime. The present invention can be used to providing an operator a simple system for obtaining the mass, multiplication, detector efficiency, and the alpha-decay-created neutron rate.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

INCORPORATION BY REFERENCE

Figure 1:
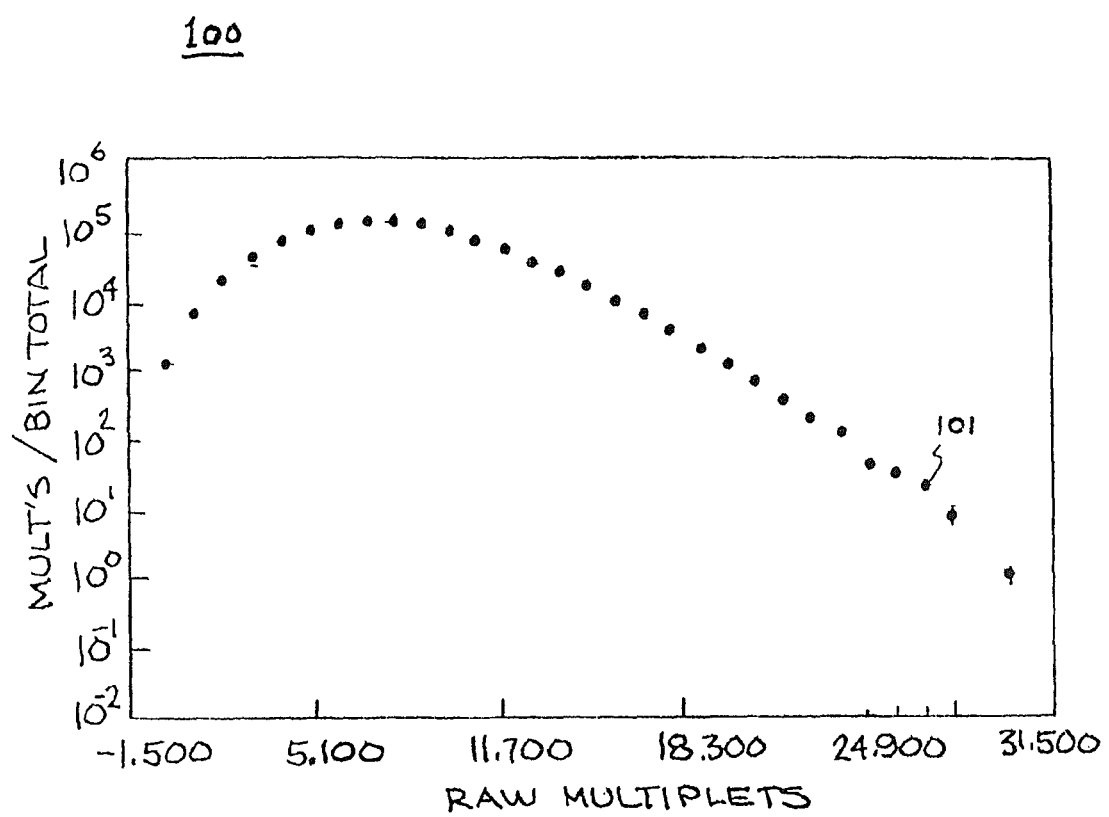
FIG. 1 illustrates an example plot of the count distribution of the frequency of neutrons from an unknown source counted in a defined duration count gate.

Each publication, patent, and/or patent application mentioned in this specification, including U.S. Provisional Patent Application No. 60/612,968 filed Sep. 24, 2004, U.S. patent application Ser. No. 11/233,228 filed Sep. 21, 2005, U.S. patent application Ser. No. 11/244,088 filed on Oct. 4, 2005, and U.S. patent application Ser. No. 12/047,297 filed Mar. 12, 2008 are herein incorporated by reference in its entirety to the same extent as if each individual publication and/or patent application was specifically and individually indicated to be incorporated by reference.

DETAILED DESCRIPTION OF EMBODIMENTS

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Fission is defined as the emission of multiple neutrons after an unstable nucleus disintegrates. For example, Pu240 decays at a rate of about 400 fissions per second per gram of Pu240 atoms. When the fission occurs, multiple neutrons are emitted simultaneously, with the number ranging from zero to eight neutrons. This simultaneous neutron emission characteristic is unique to fission. Embodiments of the present invention provide a system that utilizes a multiplicity counter and a neutron detector that is configured to detect time grouped (correlated) neutrons produced by fission sources. The present invention provides a system that utilizes a set of parameters that describe an unknown mass of fissile material. The present invention has use in providing an operator a simple system for ascertaining certain characteristics of the source, such as the mass, multiplication, detector efficiency, and the alpha-decay-created neutron rate.

As stated above, one significant characteristic of fission is that neutrons emit in groups. Random sources of neutrons are emitted with no regard for grouping, however, since the appearance of these neutrons at the detector are randomly spread in time, some may accidentally appear in close temporal proximity. An example is a neutron detector that counts neutrons for short periods of time, say ½ milli-second time periods (gate periods). This example time corresponds to a typical neutron diffusion time in a typical detector, the choice of which depends on specifics related to detector design. If the ½ msec. period is counted once, the count may be one, two, or three counts, or some other integer number, including zero. It is desirable to select an appropriate observation time, such as two to three times the typical neutron diffusion time, and then repeat the sampling of counts period many times to produce a histogram of counts described as the number of occurrences of each multiplet group. This yields a distribution of the number of times (e.g., 0, 1, 2, 3) that neutrons were observed over a number of detection periods (e.g., 10,000 repeated periods).

FIG. 1 illustrates an example plot of the count distribution of the frequency of neutrons from an unknown source counted in a 512 microsecond count gate. For the example plot of FIG. 1, it can be seen that eight neutrons were observed $10^5$ times and 25 neutrons were observed about 100 times.

Fission is unique in that it creates real correlations, while non-fission neutron sources create accidental correlations. The present invention provides a system that utilizes new developments in how fission neutron chains are modeled to simplify and remove problems related to the assay of unknown packages of fissioning material. In general, the present invention provides a system that describes the evolution of fission chains with enough detail that universal procedures can be defined for an absolute assay. The absolute assay does not need pre-defined facts or assumptions about certain detector parameters, such as the neutron detector efficiency (e), neutron lifetime (L), instrumentation dead-time losses (D), the terrestrial background (B), or the fraction of alpha-decay-induced neutrons (A). The absolute assay allows one to obtain certain source characteristics, such as neutron multiplication (M) and the mass of fissioning material (m), among other possible characteristics.

Counting neutrons by looking for time-correlated groupings is called multiplicity counting. The groupings arise from the fission process where a portion of a fission chain is detected. The analysis of this type of data assists in deriving mass, multiplication, detector efficiency, and alpha ratio (mMeA). Other factors in the analysis include neutron lifetime (L=1/), measurement gate width (T), the maximum size of neutron multiplets observed (n), the background correlation and count rate (B), and the generalized Poisson exponent ( ).

Traditionally, the count rate (singles) and the number of doubles are used to solve for up to two of the parameters, unfortunately with a significant dependence on quantitative knowledge of the other parameters. Measurement of the number of singles and doubles is limited additionally because of the necessity of incomplete sampling of the fission chains (since no one can count for an infinite time). Prior art approaches generally assume a complete sampling of the fission chain. Embodiments of the present invention provide a system that utilizes a process where the partial and full fission chain details are calculated exactly and are used to correctly interpret the measurements. The present invention provides a system that provides a solution for all of the unknown parameters listed above.

The premise of multiplication is that all neutrons in the fission chains are accounted for in the definition of nubar and multiplication (M). Nubar of the fission chain (N) and M must relate exactly (probability of fission=p) M=1/(1−pN). The first moment of the induced fission chain, started from one neutron, is (1−p)M and is what is intended to be measured. In practice the first moment is not actually measured because the populations of neutrons are always sampled incompletely. M is the multiplication defined for the full population. The measurement gives an incomplete sampling of the population and is always biased (incorrect) because of the finite sampling time. When the measured samples are biased, they no longer relate properly to the M derivation, therefore M is usually derived only approximately. The incomplete sampling problem applies to higher moments of the fission chain. These errors propagate to the other derived unknowns, regardless of how many moments are used in an analysis. Other errors arise from mistakes in understanding the matrix of unknown source containers (e.g., errors in L, A, e, and B).

The neutron counting probability distribution for a fissioning source was shown (such as by Hage-Cifarelli, H-C) to be a generalized Poisson distribution that depends on the fission chain number distribution. Embodiments of the present invention provide a system that utilizes measurements made with a multi-gate neutron multiplicity counter. A fit to the actual time dependence of the moments is used to get the proper asymptotic moments and dead-time losses inherent in the data. Since H-C$^2$ inversion leads to estimates that are biased (wrong) because of the finite sampling problem and dead-time, there are two paths to solve for the rest of the parameters. One is to use the Prasad theory to compute libraries of count distributions that may be used as a lookup table and the other is to use the H-C style estimated parameters to compute the full count distribution that would have been measured if there was no finite sampling error. The present invention provides a system that compares the truncated data moments (measurement) with untruncated and truncated theoretical moments.

The present invention provides a system that utilizes extending the moments approach to more unknowns. Also, using moments is the same as using only part of the measured data, in contrast to actually fitting the measured count distribution to a library of count distributions (theory). The present invention provides a system that fits a neutron count measurement to theoretically calculated count distributions to find the optimal set of parameters that would explain the count distribution. Fitting the full count distribution is an optimum approach because it uses all the information in the count distribution. The present invention provides a fitting approach that can extract all unknowns, in contrast to the present methods of deriving at most three unknowns from three moments. The present invention provides a system that extends the Hage-Cifarelli approach by adding a new method for dead-time correction most noteworthy for high multiplication, allows for truncation corrections, and allows direct comparison of data to parameter-based (mMea) count distributions that are generated as a proof test.

The present invention provides a system that utilizes several new steps, not all required depending on analysis objectives or measurement uncertainties. One is to create a fitting algorithm that preferentially weights the longer measurement gate width (T) periods in a fitting analysis so the short mode effects minimally alter the resulting asymptote. This is called a "T-cut" approach that prefers to extract the fundamental mode. Another method is to observe dead-time effects as a function of T, by simulation with a new count distribution calculation method. This results in multi-mode time dependences that may be specified to the data fitting process, so that the dead time (D) may be extracted. With specific time-dependence specification and understanding, the fitting routine is stable as the only free parameter is D.

In an alternative embodiment, the method specifies the time dependence in terms of the fission chain topology. This results in two modes for the second moment time dependence, and three modes for the third moment time dependence. By specifying these constrained sets of time dependences, the fitting routine will be stable as the only free parameter is the asymptote and $L_{short}$ and $L_{long}$. The present invention provides a system that utilizes computing the exact fission chain time evolution and count distribution as a function of the parameters: M, m, e A, L, T, D, and B so that the measurements can be simulated.

Regarding dead-time (D), a precursor to using count distributions for assay requires a method to add the dead-time. The present invention provides a system that utilizes distributed theoretical count distributions over time (i.e., time-tagging the count events as they would have been seen during a measurement). This is different from using a Monte-Carlo transport technique because such a technique can not sample rare events thoroughly enough. The Prasad count distribution generation technique completely fills in all rare events exactly so it can be sampled with uniform weight to form an accurate time-tagged stream of synthetic data. The present invention provides a system that utilizes random sampling of a count distribution to generate a continuous time-evolving sequence of event-counts spreads the count distribution in time, as it would be seen during the measurement. This is done by randomly initiating fission chains at a rate dependent on the source strength and sampling from an analytical theory of fission chain probability distributions to artificially create a stream of realistic data. The final step is to alter the time-tagged data with "coincidence-sum limits" to create dead time in time-tagged data or summed-count distributions. "Coincidence-sum limits" are the removal of selected time-tagged counts based on their being located within a D seconds to another count.

Embodiments provide a system that utilizes dealing with dead time when using H-C style moments based analysis. Similar to the process of generating a count distribution, the impact of dead-time is a non-linear process at the core of the count distribution generating function. Having identified the impact of dead time on count distributions, the present invention provides a system that parameterized these effects in the form of corrections to the following moments:

$$D_{cr} = T_{cr} \exp(-DT_{cr} - DT_{r2f}).$$ First moment $$D_{r2f} = T_{r2f} \exp(-D[3T_{cr} - T_{r2f}\{2T_{r3}/T_{r2f}\}]).$$ Second moment $$D_{r3f} = T_{r3f} \exp(-D[5T_{cr} - T_{r2f} + \{(2T_{cr}T_{r2f}^2 + 3T_{r4f})/T_{r3f}\}])$$ Third moment In above equations, the terms are as follows: $D_{cr}$, $D_{r2f}$ and $D_{r3f}$ are the dead-time reduced count rate, second moment and third moments; $T_{cr}$, $T_{r2f}$ and $T_{r3f}$ are the true, no-dead-time count rate, second moment, and third moments.

The process to correct moment-based dead time is to use dead-time afflicted count distributions (Applicants theory or measurements) to observe (fit) the perturbation in time dependence. Time dependences created by this method may be used to fit observed measured data to infer the amount of dead-time D. Then one may sequentially compute corrections to the moments starling with the count rate: $D_{cr}=T_{cr}\exp(-DT_{cr}-DLT_{r2f})$. Note the first iteration uses the observed data r2f. Then use $D_{r2f}=T_{r2f}\exp(-D[3T_{cr}-T_{r2f}+\{2T_{r3f}/T_{r2f}\}])$. This next step uses the observed data r3f. Next, compute $D_{r3f}=T_{r3f}\exp(-D[5T_{cr}-T_{r2f}+\{(2T_{cr}T_{r2f}^2+3T_{r4f})/T_{r3f}\})$. Note this last step uses r4f which is set equal to zero the first time through this process. Then one solves the three equations for the three unknowns. This yields a first estimate of Tcr, Tr2f, and Tr3f. This is then processed through the H-C algebra to get an estimate of mMeA. The process then computes the value of Tr4f, assuming the H-C algebra is correct. This process is repeating starting with the count rate data and using the estimated Tr4f value. The iteration continues until Tcr, Tr2f, Tr3f do not change from one iteration to the next. The final feed of Tcr, Tr2f, Tr3f into the H-C theory results in the true mMeA value.

The present invention provides a system that utilizes hundreds of time dependent gates T, such that a table of T versus L values may be measured and used as a lookup to characterize the general state of moderation in an unknown object. The general method allows one to estimate the mass of hydrogenous moderator mixed with fissioning material. This knowledge is useful for waste barrels where hydrocarbons in the presence of alpha-emitting fissile material tend to liberate hazardous gases.

The present invention provides a system that utilizes data visualization techniques that give insight into the physics and the impact of statistical fluctuations on derived quantities.

The present invention comprises the steps of counting neutrons from the unknown source and providing an absolute nuclear material assay. In one embodiment the step of providing an absolute nuclear material assay comprises utilizing a sampling method to distribute theoretical count distributions over time. In one embodiment the step of providing an absolute nuclear material assay comprises utilizing a random sampling of a count distribution to generate a continuous time-evolving sequence of event-counts by spreading the count distribution in time. In one embodiment, the step of providing an absolute nuclear material assay comprises altering time tagged data with "coincidence-sum limits" to create dead-time in time-tagged data or summed-count distributions. The step of providing an absolute nuclear material assay may comprise observing fine resolution of T axis data to obtain modal structure. In one embodiment the step of providing an absolute nuclear material assay comprises H-C Point-model extension by using constrained sums of T dependence, to select best L to fit the data which includes T-cut approach to get long-mode asymptotes, multiple mode sums to get asymptotes, and single mode fits to see deviations from single mode behavior. In one embodiment, the step of providing an absolute nuclear material assay comprises H-C Point-model extension by using constrained sums of T dependence, to select best L to fit the data which includes T-cut approach to get long-mode asymptotes, multiple mode sums to get asymptotes, and single mode fits to see deviations from single mode behavior and subsequently, use the best fit parameters from the model for analysis. The step of providing an absolute nuclear material assay may comprise dead-time correction based on T dependence perturbations/shifts. In one embodiment, the step of providing an absolute nuclear material assay comprises using L to estimate moderator mass around the fissioning material. In one embodiment, the step of providing an absolute nuclear material assay comprises pre-computing lookup tables of real-time computed count distributions for comparison to measured data.

Figure 2:
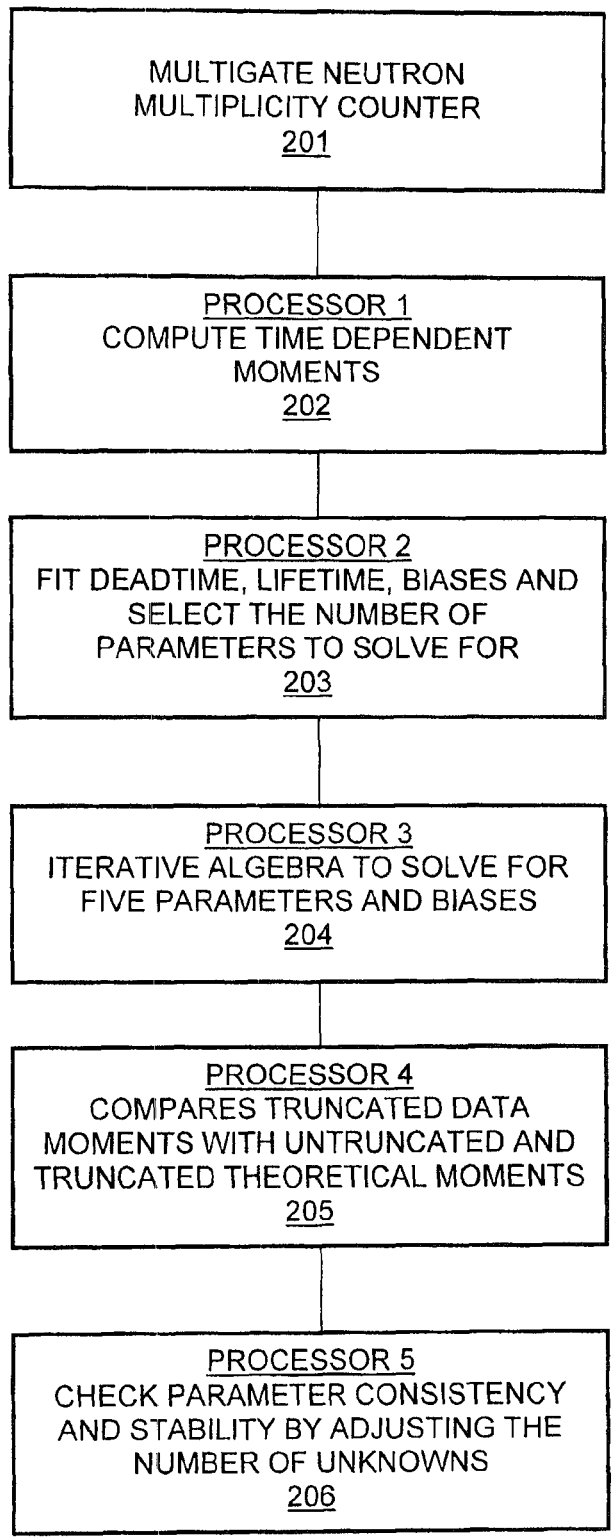
FIG. 2 illustrates one embodiment of a system incorporating the present invention.

Referring to FIG. 2, one embodiment of a system of the present invention is illustrated. The system 200 comprises a number of interconnected structural processing components. The structural components include a multigate neutron multiplicity counter 201, a first processor 202 that computes the time dependent moments, a second processor 203 that provides fits to deadtime, lifetime, biases, and allows the selection of the number of unknown parameters, a third processor 204 that solves for the unknown parameters, a fourth processor 205 that compares truncated data moments with untruncated and truncated theoretical moments, and a fifth processor 206 that checks for consistency and stability of solutions. The processors 202-206 may be separate serially interconnected processors in which the first processor is coupled to the second processor, which is coupled to the third processor, which is coupled to the fourth processor, which is coupled to the fifth processor. Alternatively, they may be interconnected in a parallel manner or mixed parallel/serial manner. In a further alternative embodiment, the processors may be separate processing functions implemented within a single processor device.

The processor or processors may be embodied in one or more central processing units (CPU) or co-processor units. The processors may be embodied entirely in one or more hardware circuits, one or more software or firmware modules, or mixed hardware/software units. The processors 202-206 may be configured to execute software commands that are provided in a memory coupled to at least one of the processors. The program or programs executed by the processors may be stored in a separate data store.

The system 200 can be used to provide an assay of nuclear material and/or to provide the amount of moderator, neutron time constant, or other biases. The process executed by processor 204 is described in tables 2 and 3 below, and the process executed by processor 205 depends on the process in table 1 below.

The present invention provides a system that relates, in detail, a correlated or uncorrelated chain of neutrons with what appears in an instrument (i.e., relates physical parameter to a measured quantity). This is in contrast to prior art systems that traditionally related how the chain of neutrons is used in a process that connects count sums to physical parameters of interest, such as multiplication. The limitations of prior art start with and are rooted in approximations in the detailed description of the neutron chain. These approximations, in the details of exactly how a chain is described and evolves in time, conspire to make the process of relating chains to physical parameters highly unstable. Prior art therefore relies on a process of calibration. For example, calibration means that of the five parameters needed to describe a physical system, four are determined independent of an assay measurement. The old assay process then proceeds by assuming the four parameters apply and are considered with a measurement of the fifth parameter, to be extracted from the assay measurement.

In the present invention, the assay solution comes from the solution of a coupled set of equations where all five parameters are used to solve for a physical parameter of interest, such as multiplication. The present invention benefits from a complete understanding of an arbitrary chain and variously allows the extraction of all five parameters, or four parameters given only one, or three parameters given only two, etc.

In the present invention neutrons are measured in a neutron detector and five parameters determine (mass, multiplication, alpha ratio, efficiency, and time constant) that describe the object that is being assayed. The present invention makes an assay for the purpose of determining these five parameters, given that the values of these five parameters are unknown.

A neutron is created by a physical process, either fission or an inducing nuclear reaction. The created neutron or neutrons then interact with the environment. If the environment contains more nuclear material (i.e., uranium), the first neutrons may create more neutrons by causing more fission or other nuclear reactions. The first and second and subsequent neutrons are the chain. A chain may start with an alpha particle creating a single neutron that subsequently creates hundreds of fissions. Another chain may start with a spontaneous fission creating three neutrons that go on to create hundreds of fissions. These chains evolve over time and some of the neutrons are absorbed or lost. Finally, some members of the chain are captured in a detector. The final captured neutrons may be counted as a simple sum or observed as a time dependent rate.

In a multiplying system undergoing spontaneous neutron emission, either spontaneous fission, spontaneous (n), or decay to a high excited state leading to neutron emission de-excitation, each source neutron can create a fission chain. The number of neutrons created in the chain corresponding to the end points of trees will have a probability distribution. Sources of fission neutrons can be statistically distinguished from random neutron sources. A random source produces a Poisson distribution, $$b_n = \frac{C^n}{n!} e^{-C} \quad \text{Equation (1)}$$

for the probability to detect a particular number, n, during a counting window, where C is the average number of counts during that counting time. A fission source produces a distribution with a larger width. Since fission chains produce multiple neutrons in bursts, the larger width, or larger fluctuation, is related to the probability to detect more than one neutron from the same fission chain.

The form of the counting distribution for a fission source is a generalized Poisson distribution. Unlike the Poisson distribution that depends on only a single time dependent parameter, C=Rt, where R is the count rate, the generalized Poisson distribution depends on many, in principle even an infinite number, of time dependent parameters, $\Lambda_k(t)$, k=1, 2, 3, .... If $b_n(t)$ is the probability to get n neuron counts in a time gate of length t, then, $$b_n = b_0 \sum_{i_1+2i_2+3i_3+\ldots+ni_n=n} \frac{\Lambda_1^{i_1} \Lambda_2^{i_2} \ldots \Lambda_n^{i_n}}{i_1! i_2! \ldots i_n!} \quad \text{Equation (2)}$$

where $i_k$ is the number of independent chains contributing k counts (for k=n, $i_n$=0 or 1, while for k=1, $i_1$=0, 1, 2, ..., n), and $$b_0 = \exp[-(\Lambda_1+\Lambda_2+\ldots+\Lambda_n+\ldots)]. \quad \text{Equation (3)}$$

For example, the probability to get 5 counts is $$b_5 = \left(\Lambda_5 + \Lambda_4\Lambda_1 + \Lambda_3\Lambda_2 + \Lambda_3\frac{\Lambda_1^2}{2!} + \frac{\Lambda_2^2}{2!}\Lambda_1 + \Lambda_2\frac{\Lambda_1^3}{3!} + \frac{\Lambda_1^5}{5!}\right) \quad \text{Equation (4)}$$

$$\exp[-(\Lambda_1 + \Lambda_2 + \ldots)].$$

If all the $L_k$ but $_1$ are zero, then $b_5 \to {}_1{}^5 e^{-1}/5!$, a Poisson distribution. The term ${}_1{}^5 e^{-({}_1+{}_2+\cdots)}/5!$ represents the probability that each of the five counts was due to an independent random source, where only a single neutron is counted from each independent chain. The term ${}_5 e^{-(1+2+\cdots)}$ is the probability that all 5 counts arise from a common source, a single chain. The term ${}_2{}^2{}_1 e^{(1+2+\cdots)}/2!$, for example, is the probability that the five counted neutrons arise from three independent random sources, two pairs of counts each have a different common ancestor, and an additional count arises from a third source. For a weak neutron source in a system of high multiplication, it is likely to get multiple counts from the same chain, but the chains are few and far between. For a strong source in a system of low multiplication, the probability of getting multiple counts from a single chain is small, while the probability of getting many counts, most from independent chains, is high. So clearly information about the source strength and multiplication are encoded in the counting distribution. It is desirable to have a complete theory relating the material and detector properties to the time dependent counting distribution. This requires a more complete theory of fission chains. Embodiments provide an analytic solution for the t→∞ fission chain, and, in the approximation that at most two neutrons are emitted in an induced fission, a closed form expression for the time evolving fission chain. These formulas apply in the point model approximation, in which spatial dependence and neutron spectrum are neglected.

Equations 2-4 above describe the transformation of count distribution $b_n$ through a process referred to as the (lambda) transform of the count distribution. The term "lambda space" may be used to refer to a resulting count distribution space.

During a detection operation, what may start out as a chain of 1000 neutrons may result in a count of two neutrons during some snippet of time, in a detector. The specific numerical process of relating the relevant physical parameters (mass, multiplication, alpha ratio, efficiency, and time constant) to an observed quantity (e.g., how many 2's) is based on approximations in the prior art. However, a more accurate and robust method of describing these chains, with all the numerical detail requires a way to relate the five physical parameters to how the chains are created. In one embodiment, a transform method (also referred to as a "Prasad transform") is used to map the probabilities to the time-dependent parameter space ($_k(t)$). This procedure provided above through Equations 2 and 3, and is summarized in Table 1 below.

TABLE 1

$x = \int_0^v e^{-\lambda(t'-t_f)}\lambda dt' = e^{\lambda t_f}(1 - e^{-\lambda t'})$, $y = \int_{t_i}^t e^{-\lambda(t'-t_i)}\lambda dt' = (1 - e^{-\lambda(t-t_i)})$, $$\Lambda_i = \left\{\int_{-\infty}^{\infty}\left[\sum_{v=j}^{\infty} P_v\binom{v}{j}(\in x)^j(1-\in x)^{v-j}\right]F_x dt_f + \int_0^v\left[\sum_{v=j}^{\infty} P_v\binom{v}{j}(\in y)^j(1-\in y)^{v-j}\right]F_s dt_f\right\}.$$

For example, the number of fives is:

$$b_s = \left\{\Lambda_5 + \Lambda_4\Lambda_1 + \Lambda_3\Lambda_2 + \Lambda_3\frac{\Lambda_1^2}{2!} + \frac{\Lambda_2^2}{2!}\Lambda_1 + \Lambda_2\frac{\Lambda_1^3}{3!} + \frac{\Lambda_1^5}{5!}\right\}$$

$\exp[-(\Lambda_1 + \Lambda_2 \ldots)].$

λ is lifetime,
t is time
ϵ is efficiency
$F_S$ is n/s (mass)
$P_v$ = f(M, v(sum))
Λ comes from a special case of a single neutron multiplying In the above table, Bn is the multiplet count in the measurement and is directly related to the five parameters with this calculation process. A multi-gate counter measures bn as a function of lifetime and neutron number. The time dependence of the $_k$ value determines the time dependent probability to get any specific number, n, of counts within a time gate, t. The scale for the time dependence is set by a detector diffusion time scale L=1/. Computing the values requires the probability distribution, $P_v(p)$ that a fission chain produces neutrons. This probability distribution is characterized by the parameter, p, the probability that a fission neutron induces a subsequent fission. The details of how $P_v(p)$ is computed is described in the report "Statistical theory of Fission Chains and Generalized Poisson Neutron Counting Distributions," UCRL-ID-1480101 (2002), authored by Prasad and Snyderman, and attached hereto as Appendix A. This provides a concise expression for the generating function for the time dependent counting distribution in terms of the generating function for the fission chain.

Since degenerate use of the procedure of the present invention is possible, in one embodiment, a Neutron Multiplicity Analysis Code (NMAC) procedure is used. This is generally similar to the Hage-Cifarelli moments approach, but the NMAC procedure extends that procedure by allowing solutions that may be truncated as all measurements are, allowing detailed time dependent analysis to better understand time truncated measurements, allowing for the inclusion of gamma-rays in the assay process, and allowing for dead time correction for the second and higher moments. The NMAC procedure is summarized in Table 2 below.

TABLE 2

NMAC solves algebra solutions based on the first 3 moments.
We always fit λ to determine neutron lifetime and therefore correct for asymptotic saturation.
This leaves four unknowns to determine: m, M, A, ε.
Case examples:

Given one unknown and R1, R2, and R3, we solve for the remaining unknowns (e.g. Given A, we solve for m, M, and ε).
Given two unknowns and R1 and R2, we solve for the remaining two unknowns (e.g. Given A and ε, we solve for m and M)

Alternatively, count distributions may be generated from first principles. Table 3 includes a discussion and process ramp-up through a process referred to as the "bigfit" process. A comparison of the NMAC procedure and the bigfit procedure is summarized in Table 3 below.

TABLE 3

Neutron Multiplicity Analysis Code (NMAC)

Mass, Multiplication, Alpha, efficiency, Lambda are unknown.
R2 = mass $[\epsilon^2 M^2 q^2(D_{2s} + M - 1(1 + A)D_2] F(\lambda t)$ and describes one of the moments of the count distribution, which is only a piece of the count distribution information.
NMAC solves algebra solutions based on the first 3 moments.
We cannot know efficiency if we don't know the geometry
We cannot solve for five unknowns with three equations (e.g. y1, y2, y3)
Higher moments algebra (y4, y5) depends too much on the tail, i.e. noisy.
Algebra involves ratios of moments, where uncertainties in the moments cause large solution errors.
BigFit Alternatively, count distributions may be generated from first principles.
Count distributions are the complete realization of the fission chain, related to all of the measured physical parameters and therefore provide all the available information and therefore the most definitive connection to the assay quantities that we want.
As a process, template fitting searches for a match between an unknown measurement and a library of variations. It appears that a library of ~4,000 variations and about $10^6$ counts is sufficient to provide a good match to the assay of the unknown.

Figure 3:
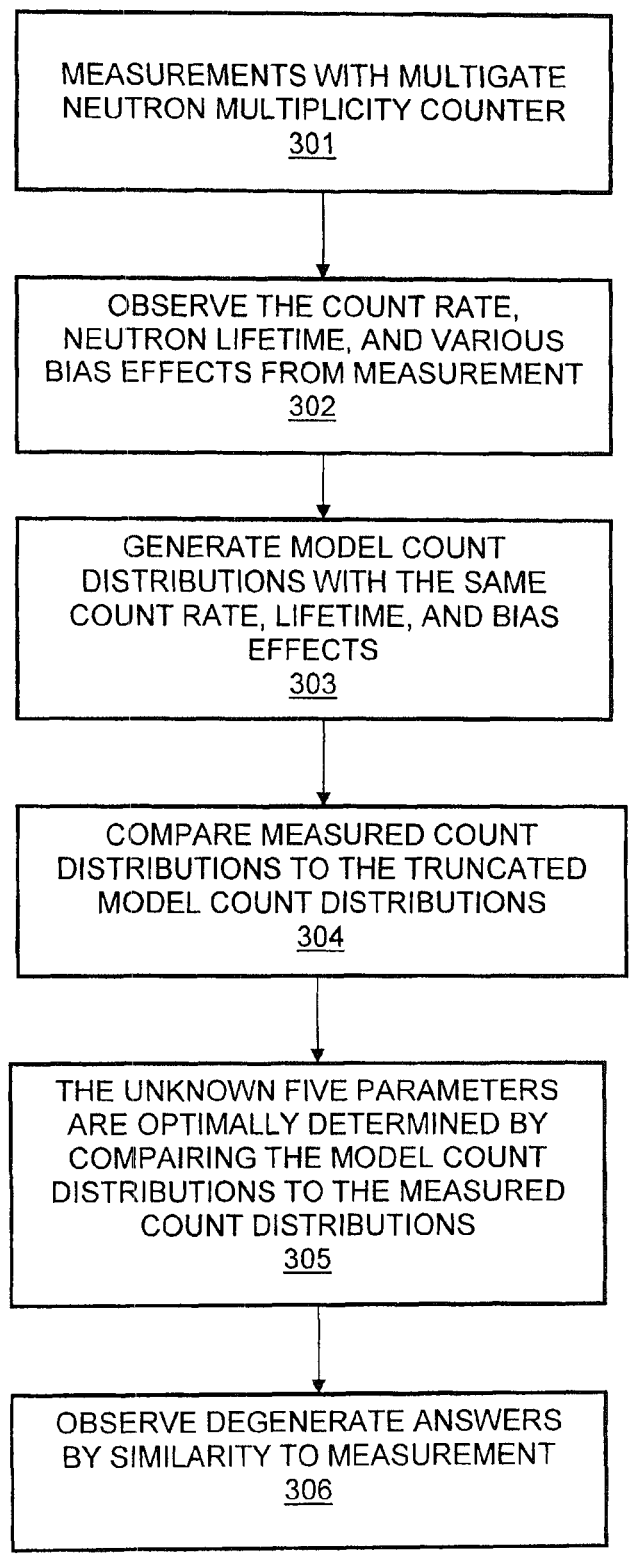
FIG. 3 illustrates another embodiment of a system incorporating the present invention.

Referring to FIG. 3, an embodiment of a system utilizing the present invention is illustrated. The system 300 provides a system for absolute nuclear material assay of an unknown source. The system 300 comprises the steps of counting neutrons from the unknown source and providing an absolute nuclear material assay. In one embodiment, the step of providing an absolute nuclear material assay comprises utilizing a sampling method to distribute theoretical count distributions over time. In another embodiment, the step of providing an absolute nuclear material assay comprises utilizing a random sampling of a count distribution to generate a continuous time-evolving sequence of event-counts by spreading the count distribution in time. In another embodiment, the step of providing an absolute nuclear material assay comprises altering time tagged data with "coincidence-sum limits" to create dead-time in time-tagged data or summed-count distributions. Dead-time is the loss of information due to coincidences in counts.

In another embodiment, the step of providing an absolute nuclear material assay comprises observing fine resolution of T-axis data to obtain modal structure. In another embodiment, the step of providing an absolute nuclear material assay comprises H-C Point-model extension by using constrained sums of T dependence, to select best L to fit the data which includes the T-cut approach to get long-mode asymptotes, multiple mode sums to get asymptotes, and single mode fits to see deviations from single mode behavior. In another embodiment, the step of providing an absolute nuclear material assay comprises an H-C Point-model extension by using constrained sums of T dependence, to select the best L to fit the data which includes T-cut approach to get long-mode asymptotes, multiple mode sums to get asymptotes, and single mode fits to see deviations from single mode behavior. The process then uses the best fit parameters from the model for analysis. In another embodiment, the step of providing an absolute nuclear material assay comprises dead-time correction based on T dependence perturbations/shifts. In another embodiment, the step of providing an absolute nuclear material assay comprises using L to estimate moderator mass around the fissioning material. In another embodiment, the step of providing an absolute nuclear material assay comprises precomputing lookup tables of real-time computed count distributions for comparison to measured data.

Referring again to FIG. 3, the method of flowchart 300 comprises step 301 measurements with multigate neutron multiplicity counter, step 302 solves three moment equations, step 303, use fit to actual time dependence of the moments to get proper asymptotic moments, step 304 uses the estimated parameters to compute the full count distribution, step 305 compares truncated data moments with untruncated and truncated theoretical moments, and step 306 makes adjustments to reduce bias. In one embodiment, these method steps are executed or performed, at least in part, in processor 203 of FIG. 2.

Measurements are made with the multigate neutron multiplicity counter 201. Three moment equations are solved with the truncated asymptotes to estimate three of the unknowns (MmeA), given one parameter. A fit to the actual time dependence of the moments is used to get the proper asymptotic moments. Since the estimates are biased (wrong) because of the finite sampling problem, embodiments of the present invention use the estimated parameters to compute the full count distribution that would have been measured if there was no finite sampling error. The truncated data moments (measurement) are then compared with untruncated and truncated theoretical moments. Adjustments to reduce bias in the moments or count distributions are then possible via a data entry window.

Figure 4:
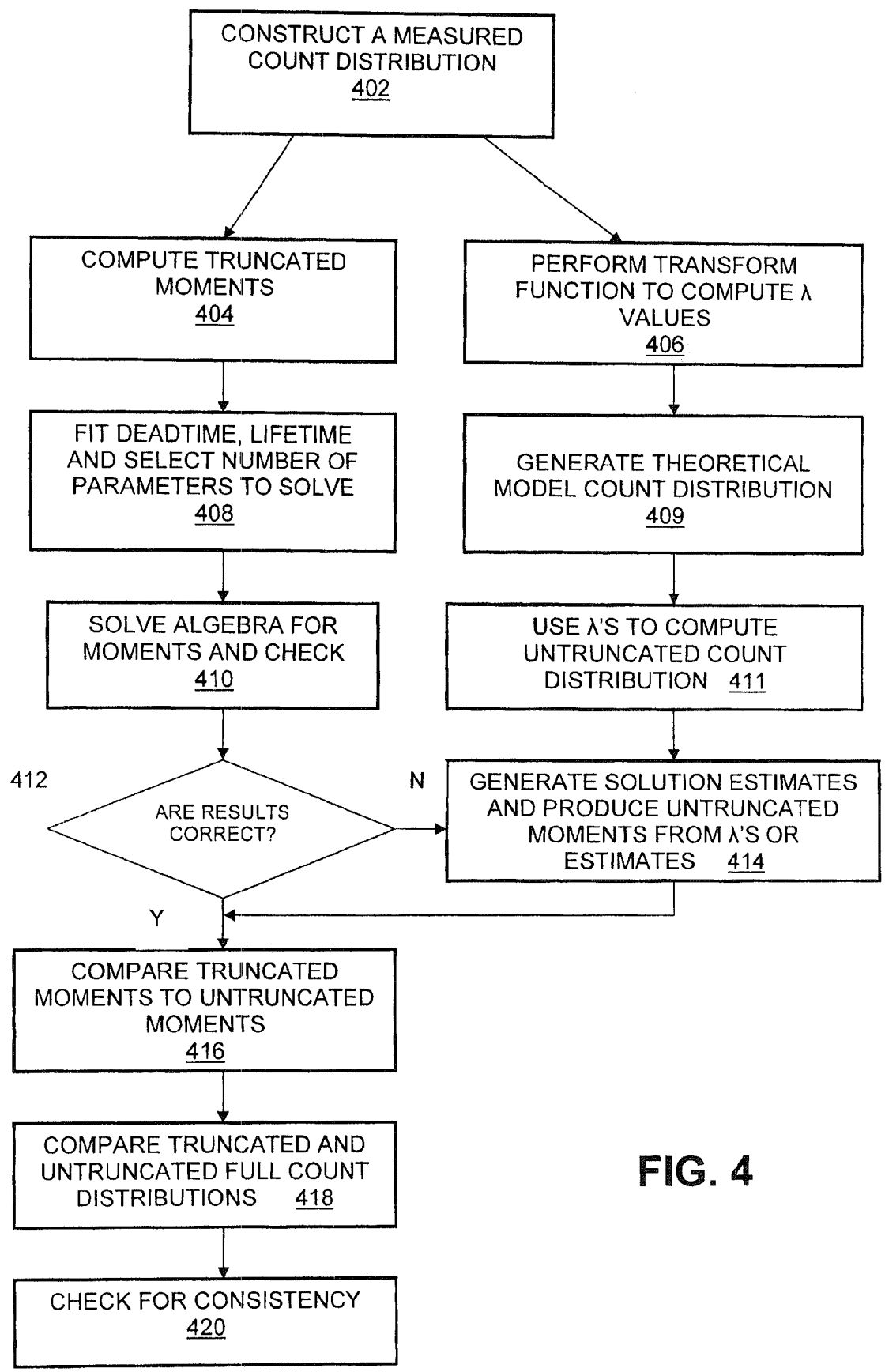
FIG. 4 is a flowchart that illustrates a method of performing an absolute nuclear assay of an unknown source, according to an embodiment.

FIG. 4 is a flowchart that illustrates a method of performing an absolute nuclear assay of an unknown source, according to an embodiment. The method utilizes the fact that the detection of pulse-trains of time-correlated neutrons can uniquely identify spontaneous fission events among neutron sources emitting neutrons that are randomly distributed in time. The count-rate of time correlated neutrons is a complex function of the mass of the fissioning material (e.g., Pu). An unknown source of fissioning material is placed in proximity of a detector. In step 402, a measured count distribution of detected neutrons from the source is constructed. The plot of FIG. 1 illustrates an example of a measured count distribution that may be generated in this process step.

In step 404, a statistical analysis operation is performed to compute certain time dependent moments. In one embodiment the time dependent moments comprise the mean, variance, skew, and kurtosis. In an embodiment, this computation can be executed or performed, at least in part, in processor 202 of FIG. 2.

The first moment (mean) can be expressed as:

$$\text{First moment} = \sum_{i=1}^{n} (x_i - \overline{X})^1,$$

The second moment is recognized as the numerator of the variance which gives information on the spread or scale of the distribution of numbers:

$$\text{Second moment} = \sum_{i=1}^{n} (x_i - \overline{X})^2,$$

The third moment is used to define the amount of skew of a distribution, which is a measure of the symmetry of the shape of a distribution (zero skew equals a symmetric distribution):

$$\text{Skewness} = \frac{\sum_{i=1}^{n} (x_i - \overline{X})^3}{ns^3}.$$

The fourth moment is used to define the kurtosis of a distribution, which is the flatness or slope of a distribution:

$$\text{Kurtosis} = \frac{\sum_{i=1}^{n} (x_i - \overline{X})^4}{ns^4}.$$

Referring back to FIG. 4, in step 406 a unique transform function is executed on the count distribution data (count distribution array) of step 402 to generate the Λ values to obtain a Λ space. This Λ space is generated by the transform procedure illustrated in Table 1. The process effectively assembles the pulses from the detector into count distributions and then performing statistical analysis and transforms on the count distribution data to generate an array of numbers representing the Λ space. This is then used to extract certain physical parameters of interest for the unknown source. The array of numbers representing the count distribution generated by step 402 is then used in conjunction with the array of numbers generated by steps 404 and 406 to set up a system of unknowns and equations to solve for the parameters of interest (e.g., three equations and three unknowns). In step 408, the process provides fits to deadtime, lifetime, biases, and allows the selection of the number of unknown parameters. In this fit step, an equation is fitted to a plot to one of the arrays of the truncated moments. This provides a deadtime parameter, a lifetime parameter, and any other desired parameter, such as bias, and so on. The parameters (e.g., deadtime, lifetime, biases, etc.) are non-linear. As shown in step 408, a choice is made with regard to the unknowns to solve for. Step 408 essentially extracts the physical parameters of interest (e.g., mass, multiplication, etc.) from the array of numbers comprising the measured count distribution. In one embodiment, an iterative process is employed to solve for these non-linear parameters. Thus in step 410, an iterative algebra process is performed to solve for the selected parameters. Typically these parameters will be the mass, multiplication, -ratio, and efficiency, although others are possible. A verification step is also performed to verify whether the solution is correct, or at least reasonable. The verification is performed by using the solutions to compute the Λ values. Thus, the verification process uses the parameters to compute the Λ values and count distribution. If the results are not correct or are unreasonable, as determined in step 412, the process generates solution estimates. The solution estimates are then used to generate untruncated moments, step 414.

With respect to the Λ space generated in step 406, a model count distribution is generated in step 409. In this manner, the non-linear measured count distribution data from step 402 is essentially transformed into a linear Λ space, which is then used to create a model count distribution. The Λ values are used to compute the full untruncated count distribution (as opposed to the truncated count distribution of step 402), step 411. The Λ values are also used to generate untruncated moments, step 414.

In step 416, the truncated moments computed in step 404 are compared with the untruncated moments calculated in step 414 from the solution estimates or the values. The moments in step 404 are truncated moments due to system limitations and inherent limitations of digital processors. Truncation issues may arise due to factors due to short count period, high multiplicity, and low detector efficiency. The process compares the truncated data moments with untruncated and truncated theoretical moments. The truncated and untruncated full count distributions are also compared, step 418. These steps compare the count untruncated count distribution provided by the Λ space with the raw count distribution data (step 402). This represents a marked improvement over prior art systems that compare truncated moments only with untruncated theoretical values. In step 420, the process checks for consistency and stability of the solutions. In this case, the solution estimate is compared with the raw data of the count distribution from step 402.

Figure 5:
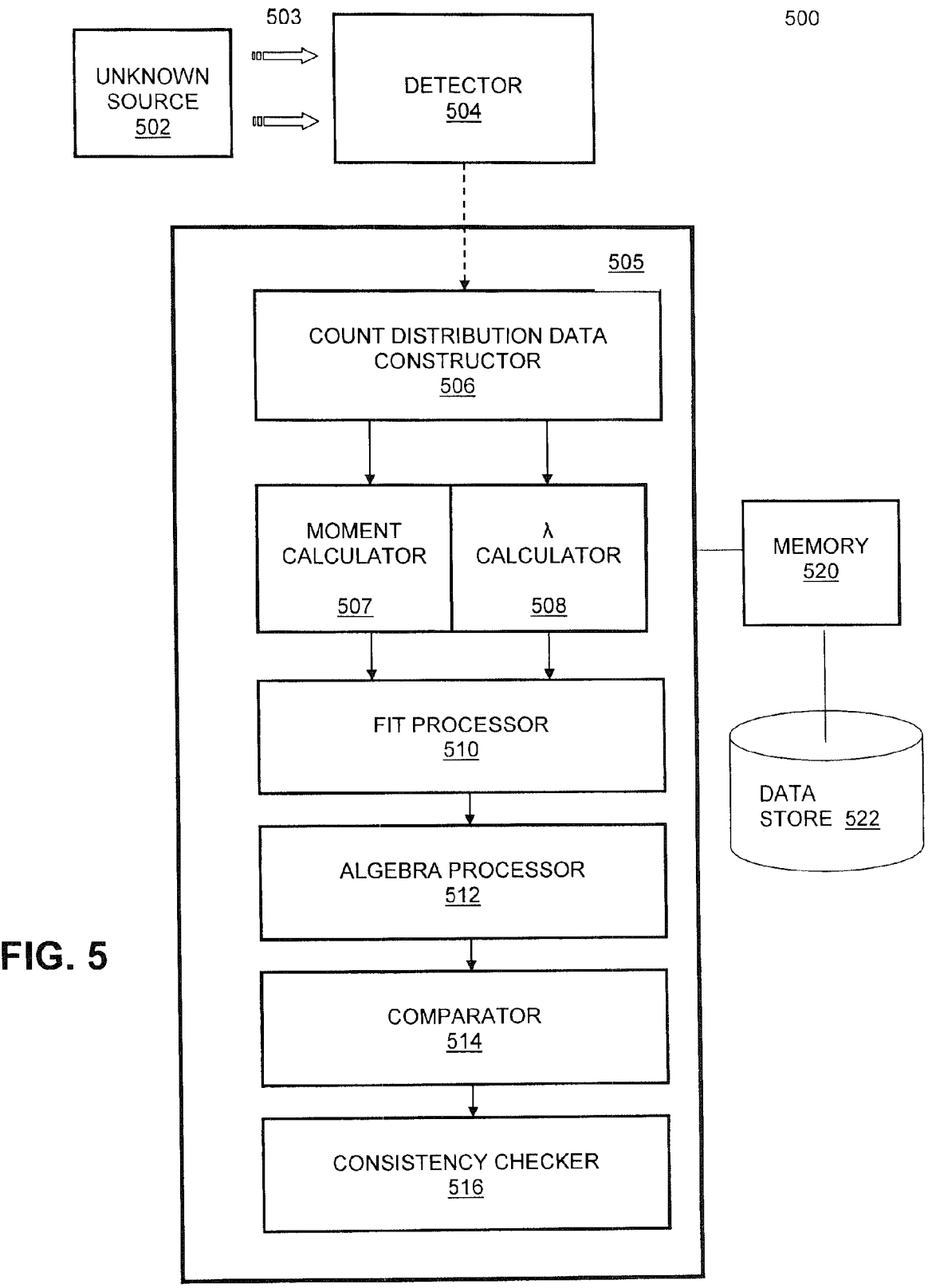
FIG. 5 is a block diagram of an absolute nuclear material assay system, under an embodiment.

FIG. 5 is a block diagram of an absolute nuclear material assay system, under an embodiment. As shown in system 500 of FIG. 5, a neutron source 502 emits neutrons that are detected by a detector 504. The neutron source 502 can be any of a variety devices that emit neutrons, irrespective of the mechanism used to produce the neutrons. Depending upon variables including the energy of the neutrons emitted by the source, the rate of neutrons emitted by the source, the size of the source, neutron source devices can be found in a diverse array of applications in areas of physics, engineering, medicine, nuclear weapons, petroleum exploration, biology, chemistry, nuclear power and other industries. Man-made sources include reactors that produce neutrons which can be used for experiments, and spallation sources that are high-flux sources, in which protons that have been accelerated to high energies hit a target material, prompting the emission of neutrons. Neutrons are used in many industrial applications. Neutron signatures also indicate the presence of fissioning nuclear material. It is generally desirable to be able to separate benign industrial neutron sources from fission sources. The neutron source may be a fissile material, and other neutron and radiation emitting sources that may present a hazard to the public. In general, the radioactive content of the source is not known (unknown source), in which case, a processing system 505 in conjunction with detector 504 is used to determine certain relevant parameters of the source in order to determine whether or not the material is fissile or non-fissile.

The neutrons 503 emitted by the source 502 are detected by detector 404. The detector may be a liquid scintillator detector or any similar type of detector. In one embodiment, the detector 504 is a neutron detector subsystem that consists of multiple moderated 7.5 atmosphere Helium-3 ($^3$He) neutron detectors. The detector subsystem includes high voltage supplies for the Helium tubes and preamplifier or discriminator units required to achieve the pick-off of the neutron events. Depending upon configuration, the detector may consist of two or more large avalanche photodiodes viewing a gas volume filled with the pressurized Helium. Neutrons are detected through scintillation of the Helium. A wavelength shifting process, such as that known to those of ordinary skill in the art, is used to measure the degree of scintillation in order to provide a measure of neutron count in the photodiodes. The detector 404 gathers the neutron data and analyzes the data for coincidences; singles, doublets, triplets, and quads up to a high order. Neutron multiplicities in various time sub-gates during each data acquisition cycles are recorded. An acquisition cycle may be defined as 512 time bins.

As shown in system 500, the processing system 505 contains a number of processing modules. The neutron detector 504 is operatively connected to a counter 506. The arrow illustrates pulses sent from the detector 504 to the counter 506. Pulses are sent to the counter 506 when neutrons are captured from the source 502.

In one embodiment, the count distribution data constructor (multiplicity counter) 506 comprises an electronic subsystem that processes the count data from the detection system. The relative time intervals between neutrons arriving at the detector are measured to build a statistical distribution of the multiplicity of the neutron detection. In one embodiment, the multiplicity counter takes each detected neutron and looks in up to 512 time interval gates to record the time interval between each neutron and others in the data stream from the detector. The counter 504 and is essentially configured to see time grouped neutrons to detect simultaneous neutrons and identify fission from the unknown source 502. In an embodiment, the counter is configured to record how many counts (group size) arrive in a ½ millisecond period, repeat this ½ millisecond recording period many times, and then plot a histogram of the number of times the different group sizes occur, such as shown in FIG. 1.

The count distribution data constructor basically generates the raw count distribution data, which is in truncated form. This data is then used by a moment calculator to calculate the time dependent moments through a statistical analysis operation, as shown in step 404 of FIG. 4. The raw data is also used to compute the values through the transform operation shown in step 406 of FIG. 4.

The deadtime and lifetime fit step 408 of FIG. 4 is performed in a fit processor 510. The simultaneous equations for the selected parameters are then solved through an iterative process using algebra processor 512. As shown in FIG. 4, the Λ values are used to generate untruncated count distributions and moments. These are compared with the truncated count distributions and moments in comparator 514. A consistency checker 516 then checks the calculated values with solution estimates. The processors 510 through 516 may be implemented in hardware through hard-wired circuitry, or they may be processors that are configured to execute software commands that are provided in memory 520. The program or programs executed by the processors may be stored in a data store 522. Alternatively, any combination of hardware and software may be implemented by the processor elements to perform the functions specified by these elements. As shown in FIG. 5, processors 510-516 may correspond to processors 203-206, respectively, under an embodiment. The program or programs comprising the software commands executed by the processors may be implemented in any appropriate language, as understood by those of ordinary skill in the art, and may codify any or all of the equations described herein as appropriate for the processing functions described in relation to FIGS. 2-5. The program may be implemented as a single program that is stored in a data store 522 for execution on the one or more processors, or it may be organized as a main program with one or more separate subprograms, each of which is stored in a specific data store and that may be executed on separate processors.

Example of Transforming a Measured Count Distribution into Lambda Space:

As an example of the transform on a given measured count distribution, assume, for a particular example, that a measured count distribution given below was measured with a 0.5 milli-second gate width:

| | |
|---|---|
| # of zero's | $10^6$ |
| # of one's | $10^3$ |
| # of two's | 10 |
| # of three's | 1 |

The number of cycles to get this data is: $10^6+10^3+10+1=1,001,011$ cycles. The number of counts in this data is $10^3+2*10+3*1=1023$ counts. The time of the measurement is 1,001,011 cycles*0.5 ms/cycle=1001.011*0.5 seconds=500.5055 seconds. The count rate for this data is 1023 counts/500.5055 seconds=2.043933 cps.

The notation $b_n$ denotes the neutron count distribution, which is the number of neutrons n (multiplets), detected within a gate period of a specific width (e.g., 0.5 ms). The gate width or gate period may also be referred to as a "counting window". Thus, $b_0$ denotes the number of zero's within the gate width, $b_1$ denotes the number of single neutrons within the gate width, $b_2$ denotes the number of double neutrons, $b_3$ denotes the number of triple neutrons, and so on. In the above example, $b_0$ is $10^6$, $b_1$ is $10^3$, $b_2$ is 10, and $b_3$ is 1.

The count distribution is normalized by setting the sum of the counts for a number of gate periods (cycles) equal to unity. Table 4 illustrates a normalized count distribution where the sum of counts for the count distribution equals one.

TABLE 4

| Multiplet counts | | normalized multiplet | |
|---|---|---|---|
| # of zero's | $10^6$ | $b_0$ | $10^6/1,001,011$ cycles = 0.99899002 |
| # of one's | $10^3$ | $b_1$ | $10^3/1,001,011$ cycles = 0.00099899002 |

TABLE 4-continued

| Multiplet counts | | normalized multiplet | |
|---|---|---|---|
| # of two's | 10 | $b_2$ | 10/1,001,011 cycles = 0.00000099899002 |
| # of three's | 1 | $b_3$ | 1/1,001,011 cycles = 0.000000099899002 |

The notation for the count distribution sum is:

$$\sum_{n=0}^{\infty} b_n = 1$$

The Lambda ($\Lambda$) values are calculated from the recursion relationships (using equations 2-4 above). Below are the three lambda values that are computed from the data in this example.

$$\Lambda_1 = \frac{b_1}{b_0} = \frac{\# \text{ one's}}{\# \text{ zero's}} = 10^{-3}$$

$$\Lambda_2 = \frac{2b_2 - \Lambda_1 b_1}{2b_0} = \frac{20-1}{2*10^6} = 9.5*10^{-6}$$

$$\Lambda_3 = \frac{3b_3 - \Lambda_1 b_2 - 2\Lambda_2 b_1}{3b_0} = \sim 10^{-6}$$

The definition of a pure Poisson (uncorrelated or random) count distribution is only a non zero $\Lambda_1$ and the other $\Lambda$'s=0. The Poisson count distribution is:

$$P_n = e^{-\bar{c}} * \frac{(\bar{c})^n}{n!},$$

$\bar{c} = \text{count} - \text{rate} * \text{time} - \text{gate} - \text{width}$, where the $\sum_{n=0}^{\infty} p_n = 1$ In this equation, $\bar{c}=\Lambda_1$ when the measured count distribution is a Poisson count source. C equals the measured source strength times the detector efficiency. However, the measured count distribution ($P_n$) is a very non-linear function of C. Transforming this distribution into $\Lambda$ space linearizes the raw count distribution data.

In general, a measurement of a correlated sum of sources (e.g. Poisson, background and fission) is described by the generalized Poisson count distribution, $b_n$, in Equation 2 and 3. This equation involves lambda values beyond $\Lambda_1$, which encodes the correlated part of the measured count distribution. It is desirable to be able to algebraically separate correlated and uncorrelated portions of the measured count distribution, including viewing the $\Lambda$ distribution as a signature of the processes that created the correlation in the radiation source. Example processes that may create correlation are fission, background from cosmic-ray spallation, or background from active interrogation where a known radiation source is added to the unknown source. Furthermore the $\Lambda$ model allows a linearly mix of sources to predict count distributions which are non-linear and directly comparable to the measured count distributions.

A method for computing the b values from the lambdas is as follows:

$b_0 = \exp[-(\Lambda_1 + \Lambda_2 + \ldots + \Lambda_n + \ldots)]$ $1*b_1 = \Lambda_1 b_0$ $2*b_2 = \Lambda_1 b_1 + 2\Lambda_2 b_0$ $3*b_3 = \Lambda_1 b_2 + 2\Lambda_2 b_1 + 3\Lambda_3 b_0$ This results in the b numbers still being normalized to a sum of one. To compare to the raw data, multiply the b values by the number of cycles in the measured unknown data. The appendix attached hereto comprises a paper entitled "Statistical Theory of Fission Chains and Generalized Poisson Neutron Counting Distributions" and provides a derivation of the relationship between the lambda space and the $b_n$ probabilities.

The purpose of breaking a neutron count measurement into lambda space is to have a different representation of the data where the count rate, the uncorrelated part of the data, and the correlated part of the data can be represented as a spectrum or histogram that describes the nature of the correlation. This leads to two novel approaches to using the $\Lambda$'s. One is to invert the measurement and compare in $\Lambda$ space. The other is to compute count distributions from $\Lambda$ space and compare the theoretical count distributions to the measurement in order to characterize the measurement.

One strategy is to use the former approach to transform a measurement of background into $\Lambda$'s. In general, this recursive transformation of data from a measured count distribution (b's to $\Lambda$'s) may be unstable. For low count rate data and near Poisson data the transformation is stable. Other data is stable subject to constraining the $\Lambda$'s to be positive.

This latter approach depends on having a model for the $\Lambda$'s for fission (table 1) and background or any other source ($\Lambda$'s obtained in the former transformation approach) we may choose to interrogate with.

This embodiment provides the advantage of transforming results in a representation of the measurement where superposition, or subtraction of, extraneous effects (e.g., background) is physically and mathematically correct.

Numerous applications that include are possible, including:
1) Separating background from a measurement, i.e. correct background subtraction,
2) Separating the correlated portion of the measurement for recognition and identification,
3) Adding to a measurement (active interrogation) a Poisson source that is separable,
4) Adding to a measurement (active interrogation) a correlated source that is separable,
5) Changing the gate width to recognize short and long time scales associated with correlation from cosmic-ray induced correlation or fission as a method of distinguishing neutrons based on the time-scale of correlation.

A first example application of the $\Lambda$ formalism is to construct a Poisson count distribution with the exact count rate of a measured unknown source and then compare the two. This application is useful when the measurement time is short and we want to know if there is significant correlation (i.e. fission) present. The idea is to test if there is any departure from Poisson. If so, the measured source has correlations possibly indicative of fission.

TABLE 5

| Measured Data | | Poisson with same count rate |
|---|---|---|
| Zero's | $10^6$ | 999,989 |
| One's | $10^3$ | 1021.95 |
| Two's | 10 | 0.5222 |
| Three's | 1 | 0.00017789 |

The second column is a Poisson count distribution at exactly the same count rate as the measured data, 2.04393 cps, so that the exact numbers of 0's 1's 2's 3's are directly comparable to the measured data. The conclusion is that the measured data is not Poisson because the multiplet counts are not the same. For example, the number of two's in the data significantly exceeds that expected from a Poisson distribution meaning the measured data is correlated. There are many ways to compare the two columns of numbers to characterize the radioactive source that was measured.

A second application of the lambda formulation is that the lambda values for the measured data and Poisson distribution may be compared:

TABLE 6

| Measured Data | Poisson |
|---|---|
| $\Lambda 1 = .001$ | $\Lambda 1 = 0.00102197$ |
| $\Lambda 2 = 9.5\ 10-6$ | $\Lambda 2 = 0$ |
| $\Lambda 3 = 10-6$ | $\Lambda 3 = 0$ |

The second column in the above table 6 is a Poisson distribution in lambda space for the exact same count rate as the measured data, 2.04393 cps. One immediate thing to note is that the data is not Poisson because it has nonzero $\Lambda 2$ and $\Lambda 3$ values.

Comparison options lead to opportunities to test for fission, background, interrogation sources, or indications of dead time which manifest as a relative deficit of correlation relative to the Poisson distribution.

To demonstrate the superposition principal a count distribution is utilized that is made of two components, Poisson and fission. From the above example, the Poisson value of 2.04393 cps and a fission value of 1.34465 cps (from the formalism in Table 1 where we set Multiplication=5, efficiency=0.04, random driver at 10 n/s, and U235 multiplier) have $\Lambda$'s that will be added. Note that the $\Lambda$'s to have been truncated to three to match the number of $\Lambda$'s in the example.

TABLE 7

| Poisson | Fission | Sum |
|---|---|---|
| $\Lambda 1 = 0.00102197$ | $\Lambda 1 = 0.000406794$ | $\Lambda 1 = 0.00142876$ |
| $\Lambda 2 = 0$ | $\Lambda 2 = 0.0000598869$ | $\Lambda 2 = 0.0000598869$ |
| $\Lambda 3 = 0$ | $\Lambda 3 = 0.000020965$ | $\Lambda 3 = 0.000020965$ |

The sum in the above table 7 now represents the $\Lambda$ values for a new count distribution that will have a count rate of 2.04+1.344 cps=3.388 cps. The equations 2-4 are used to again produce the $b_n$, values from the $\Lambda$ values.

Sum (Fission+Poisson at 3.388259 cps)
Zero's: 999484
One's: 1428
Two's: 60.87
Three's: 21.04

Since the premise was to generate an example consistent with an initial count distribution, we note the linear nature of the transform. Therefore, to construct a count distribution for the original 2.04 cps, the sum $\Lambda$ values must be scaled by a factor 2.04393/3.388259. Using the scaled $\Lambda$ values, the equations 2-4 are used again to produce the count distribution below.

Sum (Fission+Poisson at 2.04393 cps)
Zero's: 1000009
One's: 861.879
Two's: 36.4972
Three's: 12.678
Four's: 5.4317
Five's: 2.41389

This new summed and scaled count distribution represents the model of Poisson and fission. All of the computations are then used to compare with the original example so that two possible explanations of the original measured data can be provided. Table 8 provides a summary of the computed data compared to the measured data.

TABLE 8

| | Measured Data | Poisson with same CR | Poisson + fission with same CR |
|---|---|---|---|
| Zero's | $10^6$ | 999,989 | 1000009 |
| One's | $10^3$ | 1021.95 | 861.879 |
| Two's | 10 | 0.5222 | 36.4972 |
| Three's | 1 | 0.00017789 | 12.678 |
| Fours | 0 | 0 | 5.4317 |
| Fives | 0 | 0 | 2.1389 |

In table 8 above, all three data sets are at 2.04393 cps, therefore attempting to discriminate between Poisson and fission is not possible with a gross counter. Using this multiplicity formalism however, there are two hypothesized models to consider. From the explanation of the example above, it is known that the measured data is not Poisson. From the table above it can also be seen that it is not a combination of Poisson and fission at the constructed count rates. Note that the process computed extra multiplets for the sum to illustrate that with fission, there is a tail that may not be evident in a measurement because of truncation (e.g. short count times)

For purpose of illustrating the flexibility of the above described and illustrated lambda transform approach, there are many ways to use the transform algebra to construct approaches to decomposing measurements. For example, thousands of hypothetical count distributions made of many mixtures of Poisson, background, external drivers, and fission at any multiplication, mass, efficiency, alpha ratio could have been computed to use as a numerical lookup to match the measured data. Clearly, this would require working with $\Lambda$ values until the count rate of the measurement is known, in order to finalize the exact multiplets to compare with and thereafter determine which model best matches the unknown measurement.

Another example approach is to follow the above example working with the $\Lambda$ values and simply convert the measurement into $\Lambda$ values and compare sums in $\Lambda$ space, since lambda space is linear. Linear superposition in lambda space allows partitioning the lambda sums and thereby identifying the signatures of the components manifest in the measurement. Superposition in lambda space may be constrained by a regression technique to fit lambda distributions, thereby retaining the character of the original source creation process (i.e. relative ratios of $\Lambda_n/\Lambda_m$) yet allowing the count rate to be fungible and determined by the regression weights.

Another example could be to measure the $\Lambda$ value for background and use those as a fungible count rate signature to find the fraction of the total measurement that is in excess of background.

Another example could be to first do any of the above analysis on data at short gate widths to characterize the correlations, including any partitioning of Poisson, background, interrogator signal, or fission, and then perform the analysis again at a longer gate width. Any ambiguities due to truncation can then be distinguished by the different time scales associated with the prompt nature of cosmic background and the much slower fission chain evolution in multiplying fissioning material. (e.g., cosmic spallation time scales are nanoseconds and moderated fission chains evolve over micro-seconds). In other words, if the observed correlation appears in short time scales and is also present in the same amount in the longer time scale, then the correlation signal was made by a physical process that completes on the shorter time scale. Conversely, correlation that only appears on the longer time scales must not be produced by a physical process operating on the short time scale. This process, therefore can be implemented over a range of time scales to observe all physical creation time scales. These inventions do not limit to neutrons but include any process making correlated particles, such as gamma-rays, pions, electrons.

With reference to the system of FIG. 2, there are certain alternative embodiments that may be implemented. In one embodiment, an analysis component may be included in system 200 that incorporates a difference calculator that analyzes the output from the multiplicity counter 201 to determine if it is consistent with a background noise, an innocent source, or a potentially dangerous radioactive source. The analysis component includes a difference calculator, which calculates the difference between the unknown source and a standard Poisson distribution, and a graph display that displays the neutron emission distribution of the unknown source and the Poisson distribution in a superimposed graphical representation. The analysis component may perform an analysis of the neutron multiplicity data through a Feynman Variance Technique, or equivalent method.

Figure 6:
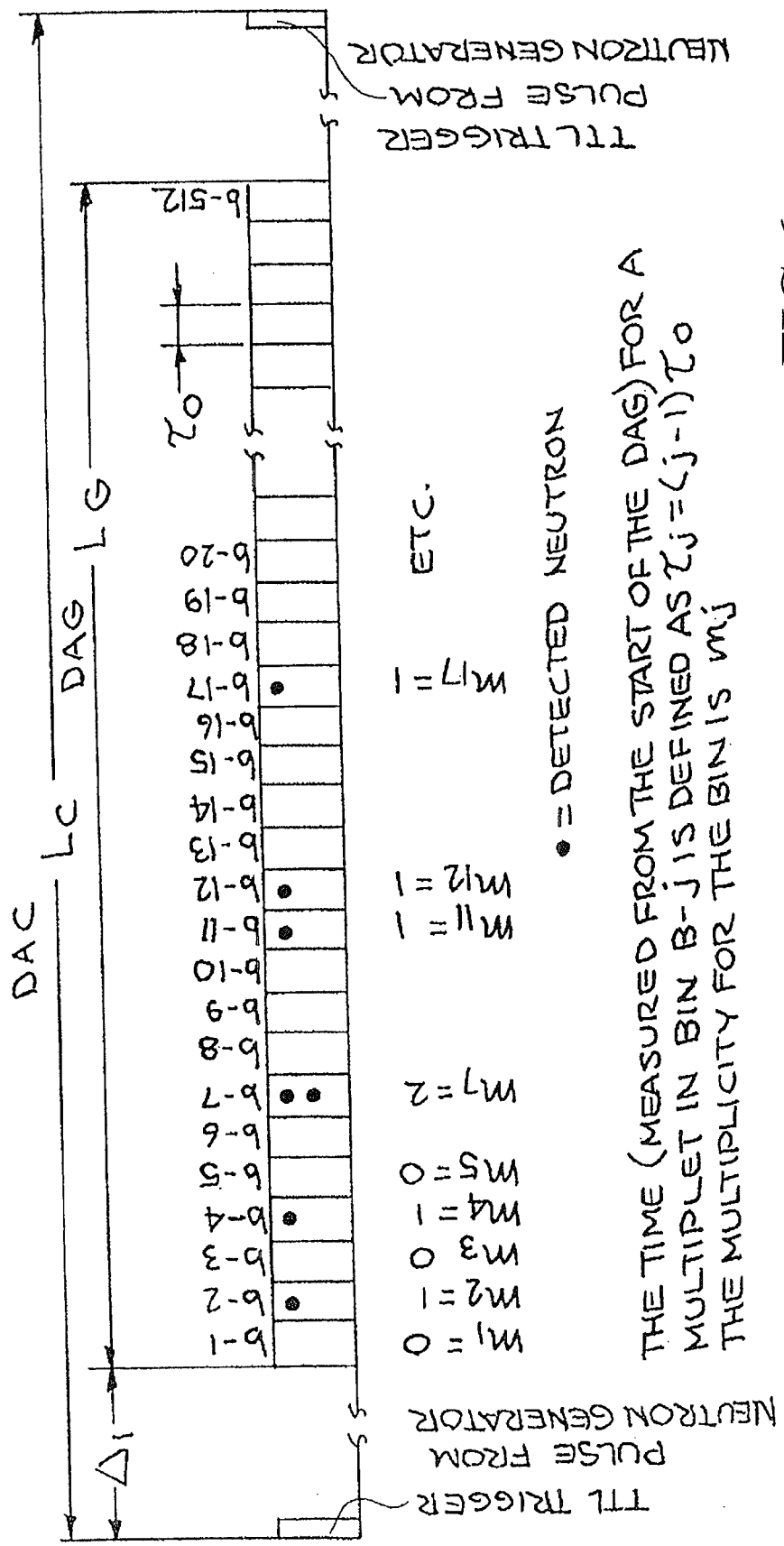
FIG. 6 illustrates the time-dependent, periodic trigger mode counter that can be used with embodiments of the assay system.

In one embodiment, the multigate neutron multiplicity counter 201 may be implemented as a real-time multiplicity counter, such as that described in U.S. patent application Ser. No. 12/047,297 filed Mar. 12, 2008, which is hereby incorporated by reference. Such a counter feeds pulses form a multi-detector array in parallel to individual inputs that are tied to individual bits in a digital word. The word is loaded at the individual bit level in parallel, and read at regular intervals with all bits read simultaneously. This word is then passed to a number of storage locations for subsequent processing. The period of typical fission occurs in the millisecond range. In one embodiment, the counter is configured to operate in short duration mode, such as 40 ns. The counter is configured to operate with a pulsed neutron source. The data acquisition cycles (DAC) are initiated either by periodic internal triggers or by external triggers and can be used for either passive measurements (such as for background analysis) or with periodic neutron generators. For this period trigger mode, a time-dependent measurement class is utilized. In this class of measurement, data are sorted according to the number of multiplets in each time bin within the data acquisition gate. These data allow one to measure the neutron die-away following the injection of the neutron pulse. This mode thus performs multiplet die-away analysis by recording the number of multiplets of each multiplicity in each time bin during each DAC comprising a single data acquisition gate (DAG). The DAG begins after an adjustable delay following the trigger and consists of 512 time bins. FIG. 6 illustrates the time-dependent, periodic trigger mode counter that can be used with embodiments of the assay system. In FIG. 6, the time, measured from the start of the DAG, for a multiplet in bin b–j is defined as: $j=(j-1)_o$, and the multiplicity of the bin is $m_j$. In one embodiment, detected neutron group sizes are tallied by arrival times. In general, fission does not result in clusters during each time period. Groups that are spread over in time are thus more likely due to fission. This can be used to discriminate against background sources.

In one embodiment, a method for compensating for background effects is provided. Background radiation generally comes from cosmic ray interactions in the detector, surrounding structures, the unknown source's non-fissile mass, or fissioning uranium in terrestrial material. One approach is to use the generating function to reverse engineer the generalized Poisson exponent values ('s) in the background. The present invention provides a system that measures background with a neutron counter device, in the presence of large masses of iron, lead, and polyethylene. Specifically, the process is to compute the natural log of the background count distribution generating function and solve for the 's. The present invention provides a system that utilizes the background as a free parameter in generating data to develop specific understanding, or to partition an unknown measurement into the fraction of background present at measurement time. This approach is technically superior since fission chains are created from the non-linear process and not simply additive environmental fissioning mass.

Figure 7:
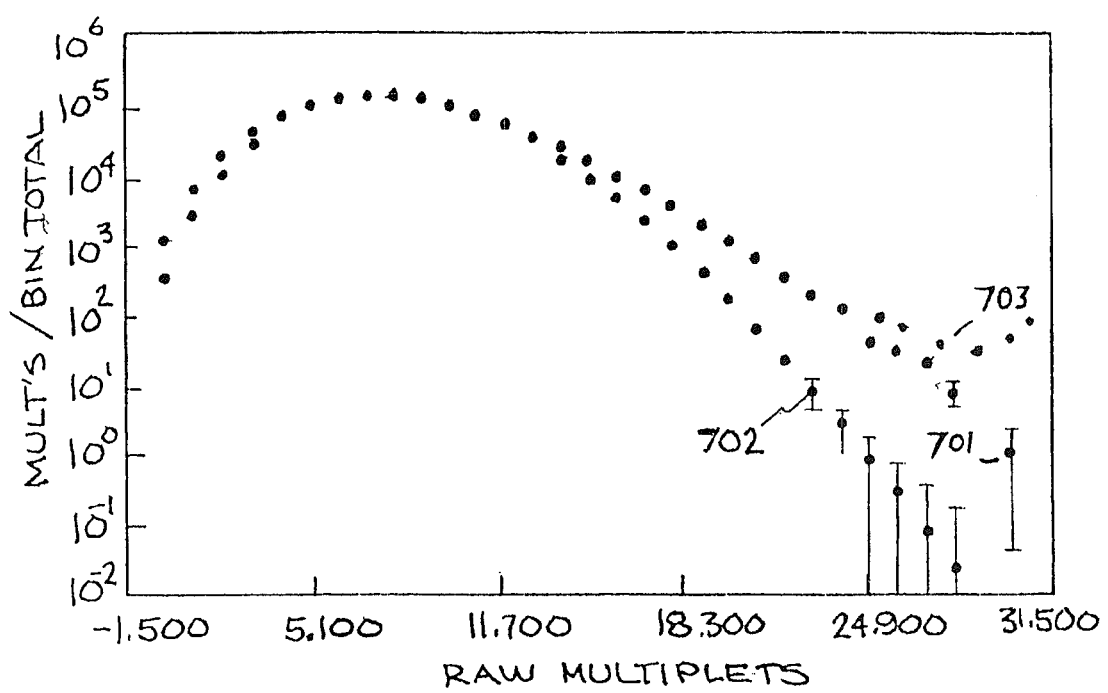
FIG. 7 illustrates a neutron distribution curve illustrating background effects of a cosmic source.

To compensate for background, the neutron detection system includes a method for allowing the filtering of background neutron noise due to other sources, such as cosmic or man-made sources. As stated above, typical background consists of single neutrons and neutron groups from multiple neutron events caused by cosmic rays. The Poisson distribution of the events will cause some random coincidence events. These random coincidences can be calculated using the singles count rate and device characteristics. FIG. 7 illustrates a neutron distribution curve illustrating background effects of a cosmic source. In one embodiment, the simple observation of a neutron distribution curve with a shape like that shown in FIG. 1 would indicate the presence of neutrons due to cosmic interference. Correlation is indicated by the presence of events with higher order multiplicity in the distribution. As shown in FIG. 7 the actual background 703 is slightly more correlated than the neutron distribution from the unknown source 701, and both are more correlated than the pure Poisson distribution 702. As shown in FIG. 7, the actual background curve 703 has a characteristic and relatively pronounced curve up at the very end of the plot. The shape of curve 703 can be used by an analyst or a program to determine whether or not the presence of neutron emission is due to cosmic effects as opposed to a potentially dangerous source.

The $\Lambda$ space count distribution is applied to provide a comparison with such background distributions. If the observed count matches derived count distribution using the $\Lambda$ transform operation, then the detected neutrons are due to background sources. Background effects generally vary over time and space. However, the system allows one to quantize the background at least within certain temporal and or spatial boundaries. This background effect can then be disassociated or filtered out of subsequent measurements.

Embodiments of the present system can also be used to detect gamma/neutron coincidence. The energy of nuclear fission is released as kinetic energy of the fission products (e.g., neutrons) and fragments, and as electromagnetic radiation in the form of gamma rays. Gamma rays typically have frequencies above $10^{19}$ Hz and therefore energies above 100 keV and wavelength less than 10 picometers. Gamma rays have the shortest wavelength of all waves in the electromagnetic spectrum and are highly penetrating. In one embodiment, the source 502 may include or comprise gamma rays that are emitted. In this case, the $\Lambda$ transform operation 406 is used to produce untruncated count distributions and moments for the gamma ray emission.

In one embodiment, a liquid or plastic scintillator may be used instead of the He3 detector described above. A scintillator is a material which exhibits the property of luminescence when excited by ionizing radiation. Luminescent materials, when struck by an incoming particle, absorb its energy and scintillate, that is, they re-emit the absorbed energy in the form of a small flash of light, typically in the visible range. In this case the neutrons emitted by the unknown source 502 produce enough energy to induce ionization. The scintillator counter may be liquid-based or plastic. A liquid scintillator uses an organic solvent, such as toluene, xylene, benzene, among others. They may be loaded with other additives such as wavelength shifters to match the spectral sensitivity range and increase the neutron detection efficiency of the scintillation counter itself. Plastic scintillators are solutions of organic scintillators in a solvent which is subsequently polymerized to form a solid. Typical plastic solvents are polyvinyltoluene and polystyrene. Plastics scintillators give a fast signal (a few ns) and a high light output.

Other detectors and associated circuitry may be used to optimize the system for particular detection requirements. For example, charged particle (− particle) detectors, surface barrier diodes, gamma-ray detectors, and so on. Analog charging (RLC) circuits and digitizers may be used to condition the count data for use by the moment and -space calculators.

Figure 8:
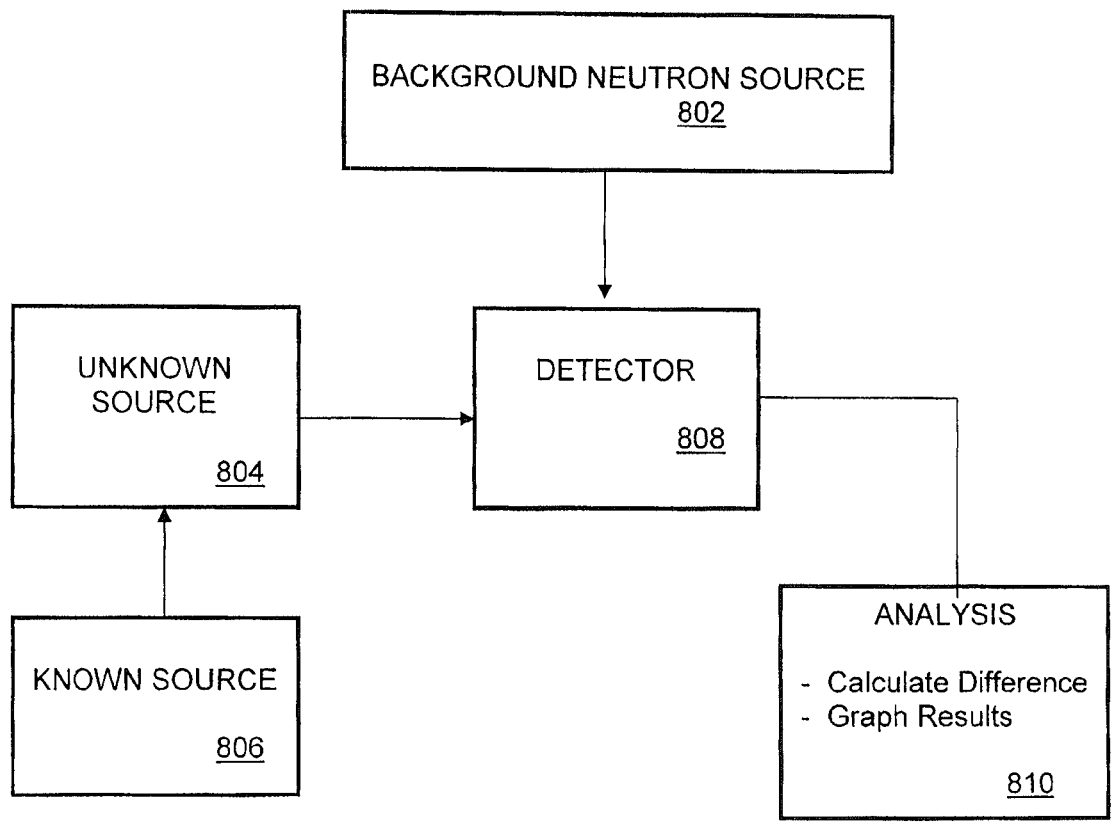
FIG. 8 illustrates a neutron detection system with an active interrogation component, under an embodiment.

In one embodiment, the detection system includes a module that allows for active interrogation of an unknown neutron source. This system includes a source of neutrons, such as Californium or Americium-Beryllium (AmBe) placed at a known distance from the unknown source. The active interrogation due to the presence of a neutron source effectively forces neutrons into the source and results in more fissions. This generally increases the speed in which the neutron distribution for the unknown source is generated. The resulting neutron distribution is then observed. FIG. 8 illustrates a neutron detection system with an active interrogation component, under an embodiment. In system 800, unknown source 804 is placed in the proximity of detector 806. The detector 806 also picks up neutron emissions from background source 802. To counteract the effects of this background noise, a known source 808 is used to drive neutrons into the unknown source 804. The resulting neutron emission distribution is then plotted relative to a Poisson distribution, and a graph, such as that shown in FIG. 7 is displayed using a graph generator. The active interrogation system of FIG. 8 can increase the strength of the unknown source above the ten to one ratio relative to the background, thus allowing greater possibility of detection from unnatural sources.

The distribution curves 701, 702, and 703 shown in FIG. 7, which may or may not include an active interrogation component, provide a graphical basis on which an analyst can view and identify man-made or environmental sources of neutrons. The difference in counts above the mean, that is, in the upper portion of each curve, along with the shape of the curve can be used to characterize the criticality of the hazard posed by an unknown source relative to the background and Poisson distributions. In one embodiment, analysis of the graphical neutron distribution data as generated by the neutron detection system can be viewed and analyzed by a human operator. Alternatively, the graphical distribution data can be further processed in a program or electronic module to provide an interpretation of the data. This module can be configured to analyze one or more parameters associated with the distribution plot such as shape, rate of rise of a portion of the curve, point-by-point differences with the Poisson and/or environmental neutron plots, and so on. Such interpretation information can be used by a user or a further response system to trigger an appropriate response to the unknown source, such as sounding an alarm, ordering an evacuation, initiating an automatic detonation sequence, or any other appropriate action.

In one embodiment, the absolute nuclear assay system may comprise part of a neutron detector that is used in a portable neutron source identification system to detect the presence of illicit radioactive material for use in homeland security applications. Such material can be used in deadly terrorist weapons such as Improvised Nuclear Devices (IND) or state-built nuclear weapons. In general, these weapons require the presence of a so-called Special Nuclear Material (SNM), that is, Uranium or Plutonium, to create a nuclear explosion. Traditional methods of detecting and identifying the presence of SNM involve the use of gamma-ray detection. These methods, however, can be defeated through the use of heavy metal shielding. The neutron detector according to embodiments augments the technique of gamma-ray detection by identifying fission neutron sources by examining the inherent characteristics of the neutron decay process. The neutron detector under embodiments includes processing and filtering components that not only count neutrons, but check the source and environmental conditions for the existence of neutron sources beyond simple noise or environmental effects. Such a detector allows for the rapid and relatively certain detection of neutron sources from potentially dangerous sources, such as INDs or similar weapons.

Aspects of the circuitry and methodology may be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: microcontrollers with memory (such as EEPROM), embedded microprocessors, firmware, software, etc. Furthermore, aspects of the memory test process may be embodied in microprocessors having software-based circuit emulation, discrete logic (sequential and combinatorial), custom devices, fuzzy (neural) logic, quantum devices, and hybrids of any of the above device types.

The processor or processors illustrated in FIG. 2 and FIG. 5 may be implemented as hardware circuitry embodied in one or more separate integrated circuit devices. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various functions disclosed, such as by the processors of FIG. 2 and FIG. 5 or in the flowcharts of FIG. 3 and FIG. 4 herein may be described using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, and so on).

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

While embodiments may be susceptible to modifications and alternates, specific embodiments have been shown by way of example in the drawings and description herein. The invention is not intended to be limited to the particular forms disclosed. Rather, the invention covers all modifications, and alternatives falling within the scope of the invention as defined by the claims.

What is claimed is:

1. An apparatus comprising:
    means for generating a measured count distribution data for neutrons emitted from a source, utilizing a defined sampling method;
    means for computing truncated statistical moments for the measured count distribution data;
    means for executing a transform function on the measured count distribution data to obtain a time-dependent parameter (lambda) space, and to generate a model count distribution;
    means for mapping probability values within the measured count distribution data to the model count distribution based on untruncated count distribution data;
    means for generating untruncated statistical moments based on the probability values;
    means for fitting an equation to a plot of the truncated statistical moments to provide at least one of a deadtime parameter, a lifetime parameter or a bias parameter, and to select one or more physical parameters of interest from the measured count distribution;
    means for performing an iterative algebraic process to compute solutions for the selected physical parameters of interest;
    means for verifying the computed solutions using parameters associated with the lambda space and the model count distribution, and generating solution estimates for the selected physical parameters if the verification reveals incorrect results for the computed solutions of the selected physical parameters;
    means for comparing the untruncated statistical moments to the truncated statistical moments;
    means for comparing the untruncated measured count distribution to the model count distribution; and
    means for comparing the solution estimates with the measured count distribution data to provide an indication of the correct solution for the selected physical parameters.

2. The apparatus of claim 1 wherein the selected physical parameters comprise at least one of five parameters associated with an absolute nuclear material assay, the five parameters including: mass, multiplication, alpha ratio, efficiency, and time constant.

3. The apparatus of claim 2 wherein the truncated statistical moments comprise mean, variance, skew, and kurtosis.

4. An apparatus comprising:
    a first processing component generating a measured count distribution data for neutrons emitted from a source, utilizing a defined sampling method, computing truncated statistical moments for the measured count distribution data, and executing a transform function on the measured count distribution data to obtain a time-dependent parameter (lambda) space and to generate a model count distribution;
    a second processing component mapping probability values within the measured count distribution data to the model count distribution based on untruncated count distribution data, and generating untruncated statistical moments based on the probability values, and fitting an equation to a plot of the truncated statistical moments to provide at least one of a deadtime parameter, a lifetime parameter or a bias parameter, and to select one or more physical parameters of interest from the measured count distribution;
    a third processing component performing an iterative algebraic process to compute solutions for the selected physical parameters of interest, and verifying the computed solutions using parameters associated with the lambda space and the model count distribution, and generating solution estimates for the selected physical parameters if the verification reveals incorrect results for the computed solutions of the selected physical parameters; and
    a fourth processing component comparing the untruncated statistical moments to the truncated statistical moments, comparing the untruncated measured count distribution to the model count distribution, and comparing the solution estimates with the measured count distribution data to provide an indication of the correct solution for the selected physical parameters.

5. The apparatus of claim 4 wherein the selected physical parameters comprise at least one of five parameters associated with an absolute nuclear material assay, the five parameters including: mass, multiplication, alpha ratio, efficiency, and time constant.

6. The apparatus of claim 5 wherein the truncated statistical moments comprise mean, variance, skew, and kurtosis.

* * * * *